US00PP09477P

United States Patent [19]

McGregor

[11] Patent Number: Plant 9,477

[45] Date of Patent: Mar. 19, 1996

[54] RED RASPBERRY PLANT NAMED 'DINKUM'

[75] Inventor: Graeme McGregor, Warrandyte, Australia

[73] Assignee: Daratech Pty., Melbourne, Australia

[21] Appl. No.: 230,113

[22] Filed: Apr. 20, 1994

[51] Int. Cl.[6] ..... A01H 5/00

[52] U.S. Cl. ..... Plt./46.2

[58] Field of Search ..... Plt./46.2

[56] References Cited

U.S. PATENT DOCUMENTS

P.P. 8,027 11/1992 Wilhelm ..... Plt./46.2

*Primary Examiner*—James R. Feyrer

*Attorney, Agent, or Firm*—Hughes, Multer & Schacht

[57] ABSTRACT

A new and distinct variety of primocane-fruiting red raspberry, characterized by its ability to product fruit of high quality and flavor suitable for the fresh fruit market. The variety is distinguished by its good fruit appearance when picked for fresh fruit sales and by its distinctly rugose leaves.

3 Drawing Sheets

SUMMARY OF THE INVENTION

The present invention is a new and distinct variety of raspberry plant named "Dinkum". Dinkum is a cross of the HRI East Mailing variety "Malling Autumn Bliss" and the SCRI variety "Glen Moy".

BRIEF DESCRIPTION OF THE FIGURES

In the drawing in which the illustrated plant parts are typical.

DETAILED DESCRPTION OF THE VARIETY

The Dinkum variety of red raspberry is characterized by its ability to produce fruit of high quality and flavor and suitable for the fresh fruit market. The variety is distinguished by its good fruit appearance when picked for fresh fruit sales, and by its distinctly rugose leaves.

The seedlings resulting from the aforementioned Malling Autumn Bliss/Glen Moy cross were grown and asexually multiplied by root cuttings at the Institute for Horticultural Development, Toolangi, Australia and tested by collaborating fruit growers in the state of Victoria, Australia. Dinkum was selected for its propensity to produce commercial yields of high-quality fruit on primocanes. Dinkum has also performed well in trials conducted in British Columbia, Canada and Kent, England.

Figure 1:
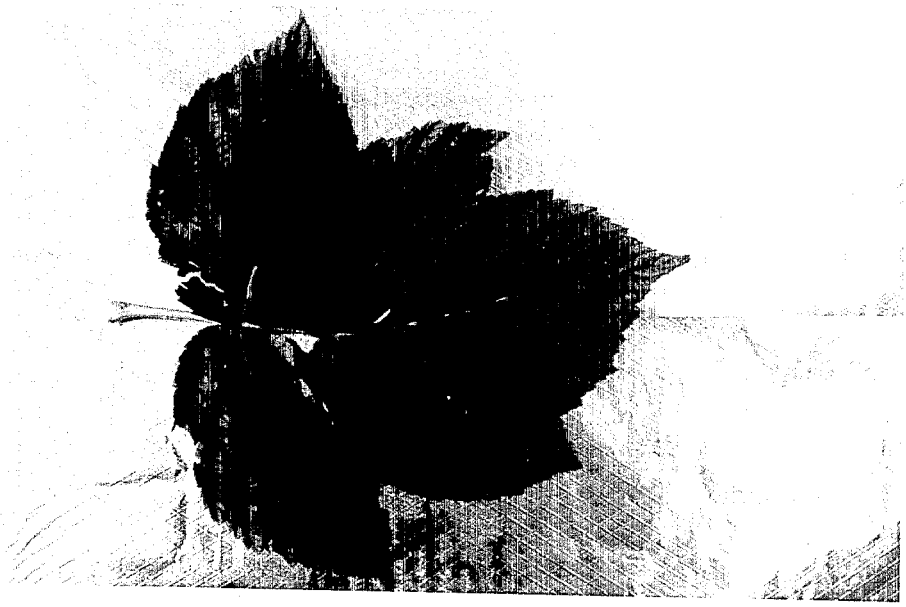
FIG. 1 show a leaf of the Dinkum variety of red raspberry.
Figure 2:
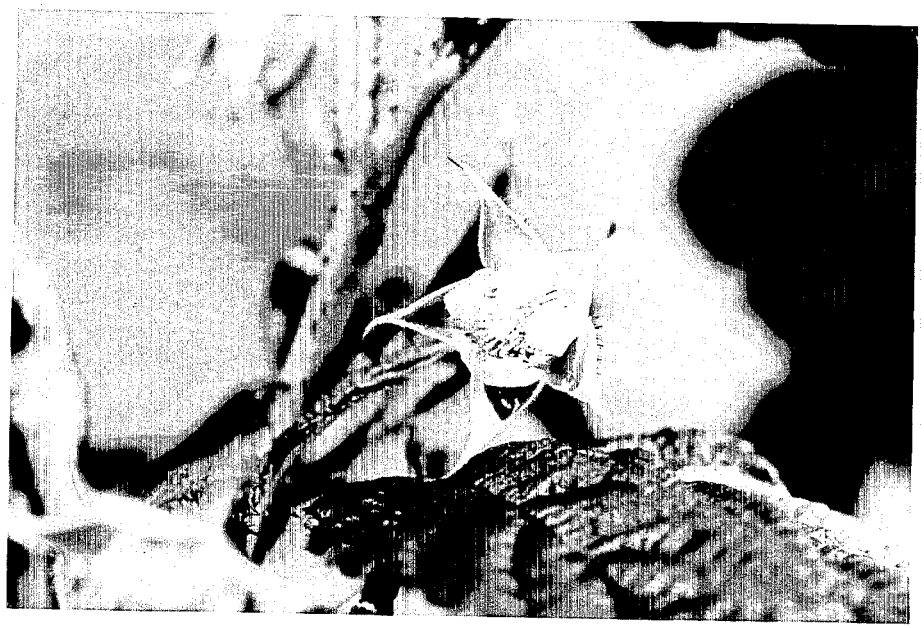
FIG. 2 shows a flower of the variety.
Figure 4:
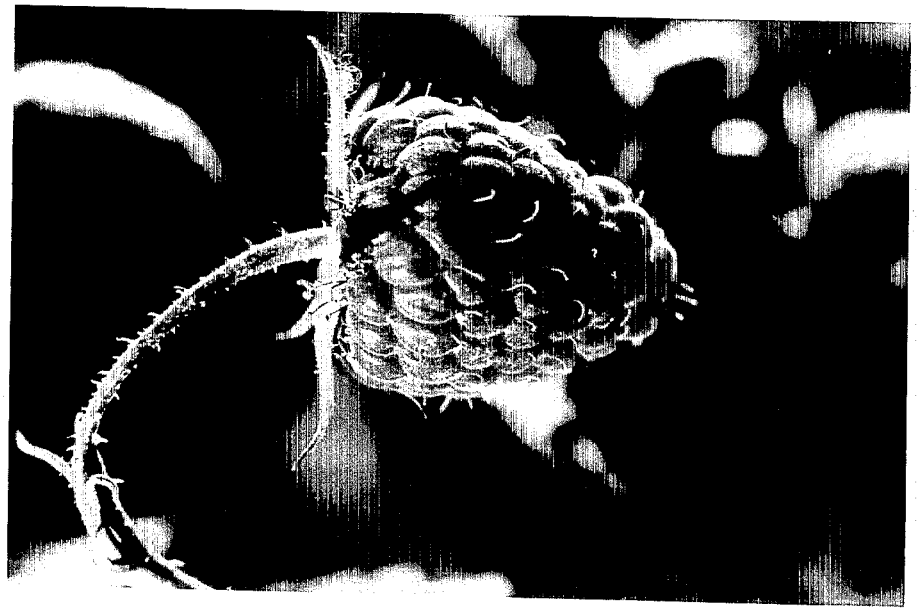
FIG. 4 shows the mature fruit of the variety.
Figure 3:
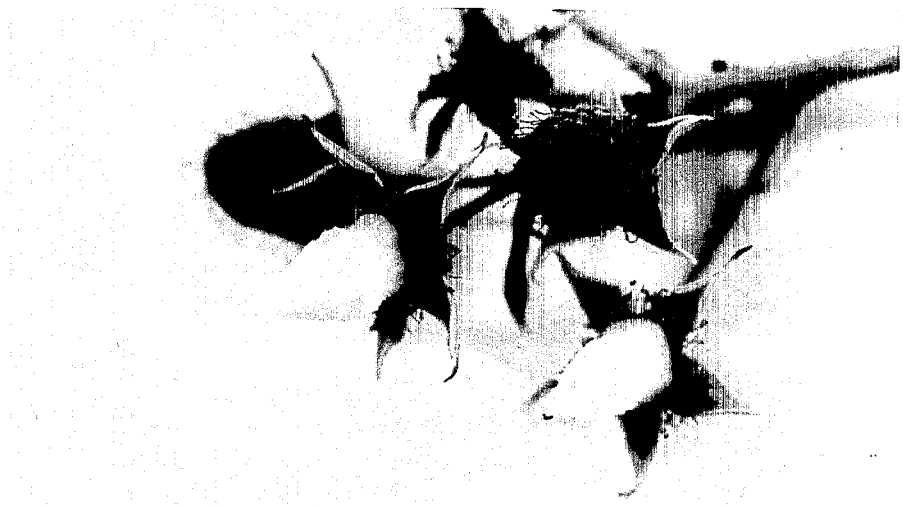
FIG. 3 shows the immature fruit of the variety.
Figure 5:
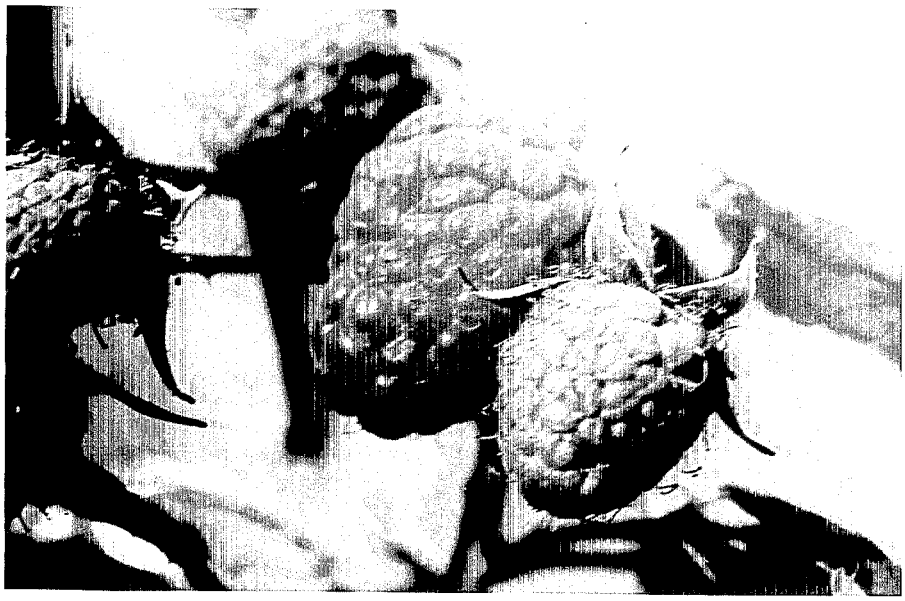
FIG. 5 shows a part of a branch bearing both ripened and unripened fruit.
Figure 6:
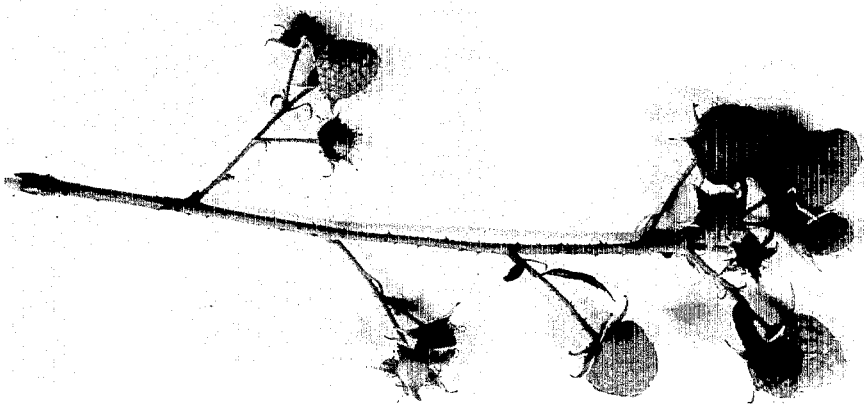
FIG. 6 shows a branch bearing ripened and partly ripened fruit.

FIGS. 1–4 illustrate plant parts of the new variety, the illustrated plant parts being typical in size, shape and color.

Leaves

Mature leaves are 5 -foliate, although one of both of the distal pair of leaflets. Leaf margins are doubly serrate and without hairs or glands. Stipulus are always present. All leaves are distinctly rugose, whereas the mature leaves of Bliss become flattened. The upper surfaces of Dinkum leaves lack hairs or other protuberances; lower leaf surfaces bear a dense tomentum. Senescing leaves in autumn turn yellow without any distinctive tints. Petioles are less densely armed than canes, have red prickles, and bear one adaxial groove. Petioles are the same color as the canes. Petiole length varies from 30 mm when new leaves first expand to 80 mm on fully mature leaves. The length:width ratio of the leaflets is 1:0.62 (standard deviation 0.03). The full length of leaves from axil to the tip of the terminal leaflet varies from 100–200 mm on newly expanded leaves to 200 mm on fully mature leaves. Petioles are 2–3 mm in diameter. Leaves are deep green above (Munsell 7.3GY 4.2/3.8) and paler grey-green below (2.4G 6.9/1.9).

Canes

Canes are uniform pale green, stout, strongly erect, and self-supporting until the fruits englarge. Color is usually 5.2GY 7.9/5.9. Red tints are occassionally formed on regions more exposed to full sunlight. The cane surface is smooth and without ridges or irregularities. Pedicels, peduncles, canes, and the basal portion of the sepals are all armed with small, dark red prickles; petioles are armed with a single distal row of prickles. Prickle color ranges from 2.4R 4.1/9.5 in immature cane to 2.7R 4.02/6.0 in fully mature cane. Cane diameter is usually equal to that of Bliss and Heritage (typically 9 mm).

Vigor is moderate; primocanes attain a greater height than Bliss but are not as tall as Heritage (typically 1500 mm compared to 1400 mm for Bliss and 1900 mm for Heritage). Cane number or density is between that of Bliss and Heritage (typically 20 canes per meter, compared to Bliss— 15–18 canes per meter— and Heritage — 25 canes per meter—, when managed in 100 mm wide rows). Sucker production is greater than Bliss, but not as aggressive as Heritage. Canes are unbranched.

Inflorescence

Leaf axils bear one, or less commonly two, peduncles (laterals), the primary peduncle bearing up to 12 flowers and the secondary peduncle bearing 1–3 flowers. Peduncles are shorter than the peduncles of Bliss (typically 130–150 mm maximum). Flowering commences early (as early as Bliss) and approximately one month earlier than Heritage. The time from 5 percent flower to 95 percent flower is usually 35 days. Petals are white. Stamens are retained until harvest. Pedicels and peduncles are armed less densely than canes, with smaller prickles. The Calyx bears very soft prickles.

Fruit

Fruit are round — conic, deep brick red at optimum maturity (Munsell 2.5R 4.5/10). Harvested fruit have a uniform color and appearance; gloss is similar to Willamette, being more glossy than Bliss but less glossy than Heritage. Individual drupelets do not appear prominent; fruits have a smooth appearance. Bloom is white, sparse and inconspicuous. Drupelets of Dinkum are not grooved, and the connection between drupelet and style is short and tapered. Individual drupelets of Bliss are grooved when ripe, either across the apex where the style enters the drupelet, or continuing across the apex and down the external surface of the drupelet. Fruit consists of 100–110 drupelets. Drupelet coherence is not significantly different from that of Bliss and Heritage (as measured by the force required to pull fruit apart). Styles are retained until harvest; some are dislodged during harvest. The torus of Dinkum is uniformly conic, smooth, and without projections. The fruit cavity is smooth and dry, without skin tearing or juice exudation.

Dinkum commences harvest either with Bliss or slightly later (in Southern Austrialia, late Jan./early Feb.).

Season length ranges from 30 to 60 days depending on the prevailing climate. The number of picks depends on commercial and economic imperatives; however, 95 percent of the crop can be harvested in seven picks whereas the same proportion of a Bliss crop requires 12 picks.

Mean fruit size is not significantly different from that of Bliss but is more variable. Fruit size is greater at the start of harvest and smaller at the end of harvest than the fruit of Bliss. Harvest concludes earlier than Bliss by days or weeks, depending on temperature.

Bliss and Dinkum fruit of equal stages of ripeness show similar susceptibility to grey mold caused by *Botrytis cinerea;* however, the fruit of Dinkum can be hand-harvested at an earlier stage of maturity then can the fruit of Bliss. Firm-ripe fruit can be picked readily and quickly. This feature confers greater shelf life on Dinkum through greater resistance to post-harvest rots, plus a lighter and more glossy appearance immediately post-harvest. Shipping quality of Dinkum is greater than Bliss due to its ability to be harvested at the firm-ripe stage, and both shipping and keeping quality are equal to Heritage. The flavor of Dinkum is considered excellent and rated higher than that of Bliss; the flavor of Dinkum is sweet and richly aromatic with raspberry esters typical of the flavor associated with Lloyd George or Willamette. Ripe fruits have a juicy texture; seeds are not prominent.

Plants

Plants do not show significantly different disease resistances than Bliss; both are susceptible to root rots and Raspberry Bushy Dwarf Virus infection and moderately resistant to leaf rust caused by *Phragmidium rubi-idaei.*

I claim:

1. The new and distinct variety of raspberry plant described and illustrated herein and identified by the characteristics enumerated above.

* * * * *